(12) United States Patent
Bryan

(10) Patent No.: US 10,383,760 B2
(45) Date of Patent: Aug. 20, 2019

(54) THERAPEUTIC DENTAL APPLIANCE

(71) Applicant: Bryan Ramp, LLC, Elkhart, IN (US)

(72) Inventor: Norman E. Bryan, Elkhart, IN (US)

(*) Notice: Subject to any disclaimer, the term of this patent is extended or adjusted under 35 U.S.C. 154(b) by 575 days.

(21) Appl. No.: 15/228,316

(22) Filed: Aug. 4, 2016

(65) Prior Publication Data

US 2018/0036164 A1    Feb. 8, 2018

(51) Int. Cl.
*A61F 5/56* (2006.01)
*A61C 7/08* (2006.01)

(52) U.S. Cl.
CPC .............. *A61F 5/566* (2013.01); *A61C 7/08* (2013.01); *A61F 2005/563* (2013.01)

(58) Field of Classification Search
CPC ...... A61F 5/566; A61F 5/56; A61F 2005/563; A61F 5/58; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61C 7/08; A61C 19/063; A61B 5/4547; A61B 5/4552; A61B 5/4557; A61B 5/682; A61B 5/0534; A63B 71/085; A63B 2071/086; A63B 2017/088; Y10S 602/902; A61N 2/00; A61N 2/002; A61N 2/004; A61N 2/006; A61N 2/008; A61N 1/40; G09B 19/003; G09B 23/28; Y10T 29/49826

See application file for complete search history.

(56) References Cited

U.S. PATENT DOCUMENTS

| | | | | |
|---|---|---|---|---|
| 3,871,370 A * | 3/1975 | McDonald | ............... | A61C 7/08 128/860 |
| 4,848,365 A * | 7/1989 | Guarlotti | ............. | A63B 71/085 128/859 |
| 4,997,182 A * | 3/1991 | Kussick | .................... | A61F 5/58 128/861 |
| 5,092,346 A * | 3/1992 | Hays | ........................ | A61F 5/566 128/848 |
| 5,592,951 A * | 1/1997 | Castagnaro | ............. | A61F 5/566 128/848 |

(Continued)

*Primary Examiner* — Tarla R Patel
(74) *Attorney, Agent, or Firm* — Botkin & Hall, LLP

(57) ABSTRACT

A dental appliance having an arch plate with a chewing surface portion and a tooth contacting surface thereon. An interior and exterior sidewall extend upwardly from the tooth contacting surface. The inner sidewall, outer sidewall, and tooth contacting surface define a tooth receiving cavity that is adapted to complementarily receive teeth on an arch and fix the appliance with respect to those teeth. An outer surface is located opposite to the tooth contacting surface and defines a plane formed by high points thereon. A tongue pocket is affixed to an anterior end of the arch plate and it has an upper and lower portion. The upper portion is integrally connected with inner sidewall and the lower portion is opposite to the upper sidewall. The tongue pocket is concave on its inner surface and on its lower portion has outer ramped surface. The outer ramped surface terminates in an incisal step.

8 Claims, 4 Drawing Sheets

(56) References Cited

U.S. PATENT DOCUMENTS

| | | | | |
|---|---|---|---|---|
| 5,915,385 | A * | 6/1999 | Hakimi | A61F 5/566 128/848 |
| 6,408,851 | B1 * | 6/2002 | Karell | A61F 5/566 128/848 |
| 6,837,246 | B1 * | 1/2005 | DeLuke | A61F 5/566 128/860 |
| 7,451,767 | B2 * | 11/2008 | Keropian | A61F 5/566 128/848 |
| 7,607,439 | B2 * | 10/2009 | Li | A61F 5/566 128/846 |
| 7,730,891 | B2 * | 6/2010 | Lamberg | A61F 5/566 128/848 |
| 7,770,582 | B2 * | 8/2010 | Chen | A61F 5/566 128/848 |
| 8,074,658 | B2 * | 12/2011 | Kittelsen | A63B 71/085 128/846 |
| 8,505,540 | B2 * | 8/2013 | Vaska | A61F 5/566 128/848 |
| 9,808,371 | B2 * | 11/2017 | Summer | A61F 5/566 |

* cited by examiner

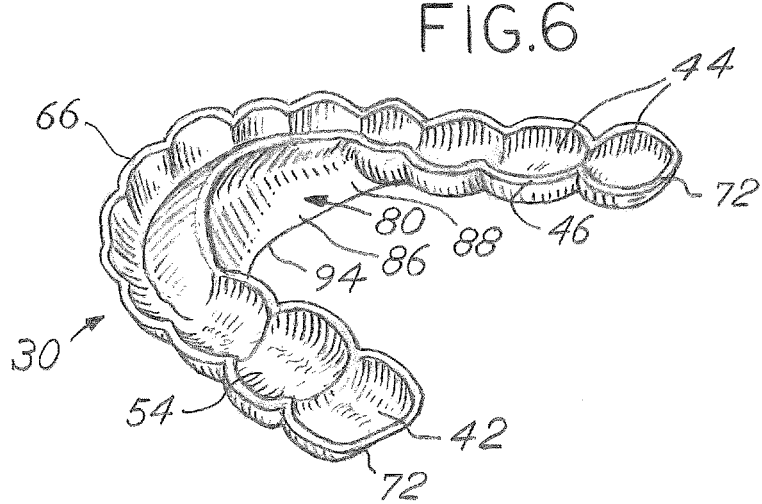
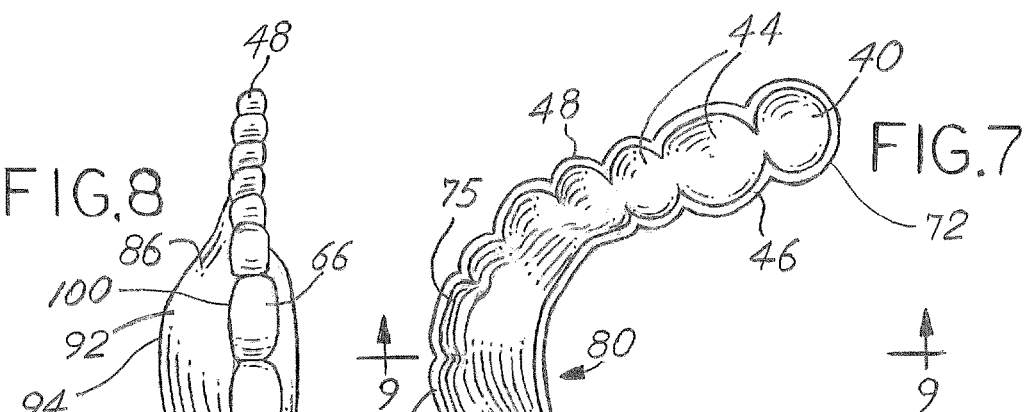
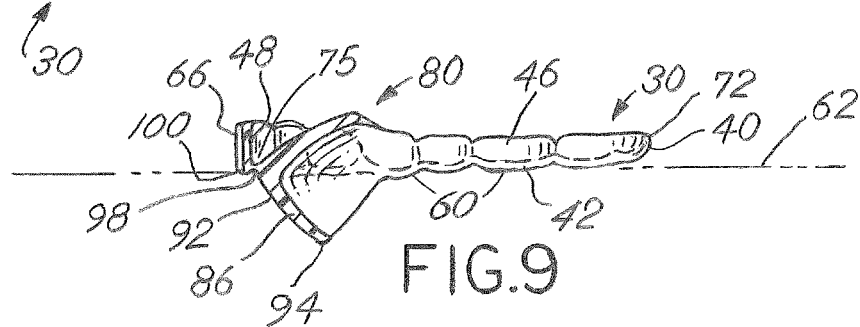

THERAPEUTIC DENTAL APPLIANCE

BACKGROUND OF THE INVENTION

Sixty four million (20%) Americans suffer from nocturnal bruxism, clenching and parafunction that deteriorates the dentition and compromises the supporting structures i.e.: periodentition, musculature and TMJ's. This results in many of the following symptoms:

1) Wear facets on dentition, fractured teeth or restorations and abfractions;
2) Subluxation of dentition leading to reduced vertical dimension, overbites, and mandibular crowding;
3) Osteoarthritis of the TMJ's, crepitus, and displaced discs;
4) Mandibular and maxillary tori;
5) Myofacial pain, temporal headaches, tendinitis, and limited range of motion in jaw opening;
6) Cervical stiffness, pain, and limited range of motion;
7) Ear itchiness, pain, and tinnitus; and
8) Morning vertigo or dizziness.

Unabated, these symptoms along with other factors like trauma, malocclusions, missing teeth or congenital proclivities can degenerate into debilitating pain and severely dysfunctional TMD that often have a very poor prognosis. The dental appliance of this invention is designed to mitigate this progressive deterioration from nocturnal bruxism, clenching and parafunction. This custom made antibruxing appliance eliminates posterior occlusion, anteriorly repositions condyles, prohibits parafunction and lateral excursions and promotes proper tongue position.

SUMMARY OF THE INVENTION

The present invention has an arch plate that has a chewing surface portion with a tooth contacting surface. An interior sidewall and an oppositely spaced exterior sidewall extend away from the chewing surface portion. The inner sidewall and outer sidewall with the tooth contacting surface cooperate to define a tooth receiving cavity that is adapted for complementarily receiving teeth on a first arch in a mouth. The tooth receiving cavity effectively affixes the arch plate with respect to the teeth on the first arch. An outer surface of the chewing surface portion defines a plane formed by high points on an outer surface of the chewing surface portion. The tooth receiving cavity has an anterior end that is adapted to receive front teeth on the first arch and posterior ends adapted to receive back teeth of the first arch.

A tongue pocket is affixed near the anterior end of the arch plate. The tongue pocket has an upper portion and a lower portion. The upper portion is connected to the inner sidewall. The lower portion extends oppositely of the sidewalls beyond the plane defined on the chewing surface portion. The tongue pocket has an inner surface that is concave. The tongue pocket has an outer ramped surface on its lower portion opposite the inner surface of the tongue pocket. The outer ramped surface is convex across the plane defined by the outer surface of the chewing surface portion. The outer ramped surface is also convex in a direction perpendicular to the plane defined by the outer surface of the chewing surface portion. The outer ramped surface terminates opposite the anterior end of the tooth receiving cavity.

BRIEF DESCRIPTION OF THE DRAWINGS

FIG. 6 is a perspective view of the dental appliance shown in FIGS. 3-5 with the tooth receiving cavity showing;

FIG. 7 is a top view of the dental appliance shown in FIG. 6;

FIG. 8 is a front view of the dental appliance shown in FIG. 7;

FIG. 9 is a sectional view of the dental appliance taken about the line 9-9 in FIG. 7;

DETAILED DESCRIPTION OF INVENTION

Figure 1:
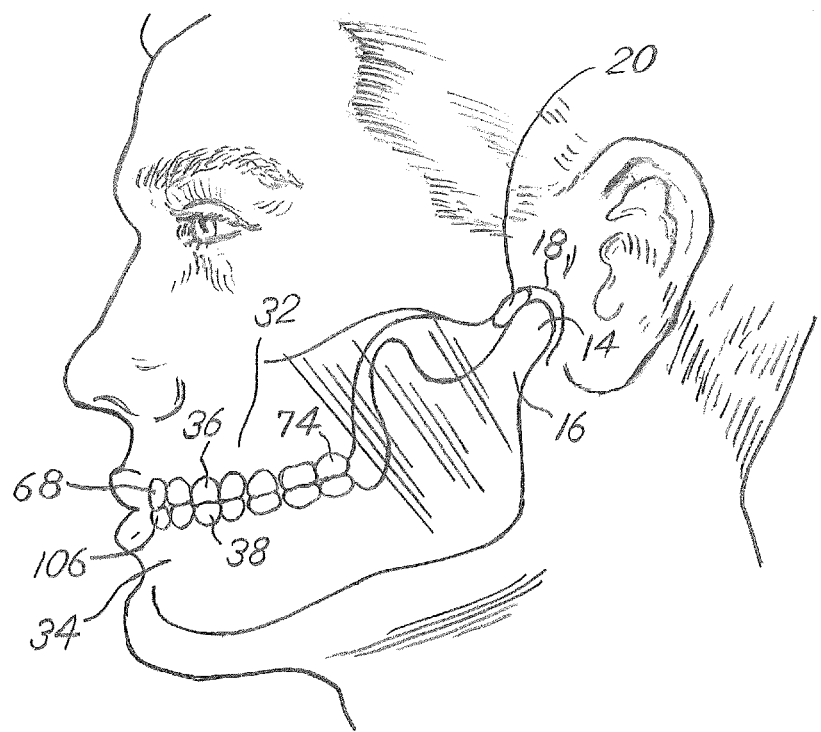
FIG. 1 is a partial sectional view of a TMJ with the jaw being closed showing a health and properly located mandibular condoyle.

FIG. 1 shows a healthy jaw and TMJ 12. The TMJ 12 is formed by a mandibular condoyle 14 that forms a ball at the end of the mandible bone 16. The condoyle 14 rests in an articular fossa 18 that forms a complementary socket to the condoyle 14. The condoyle 14 is cushioned by an articular disc 20 made of cartilage that allows the jaw to hinge relatively freely when properly aligned as shown in FIG. 1.

Figure 2:
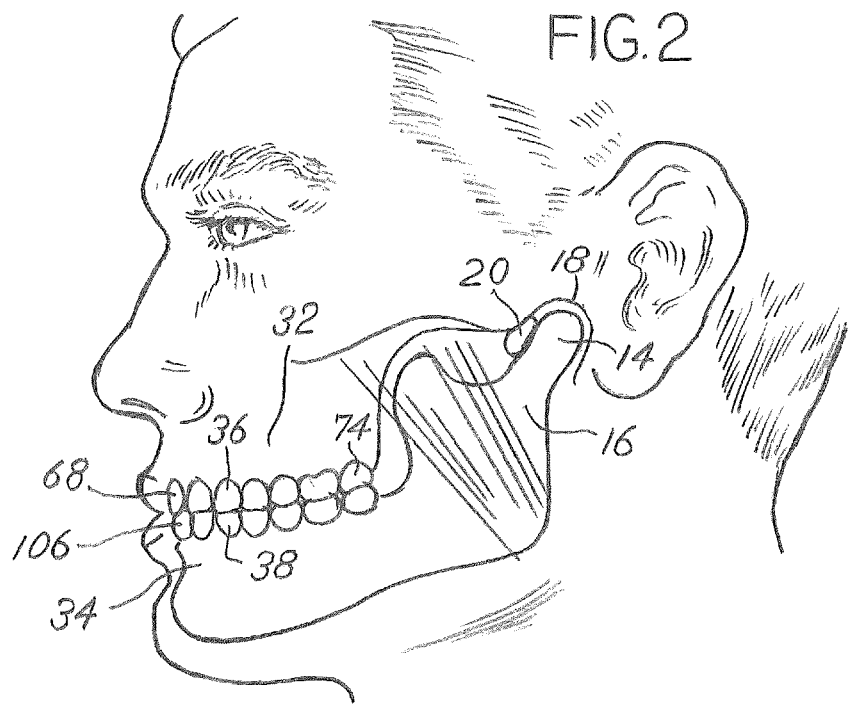
FIG. 2 is the partial sectional view similar to that shown in FIG. 1 of a TMJ with the mandibular condoyle displaced and the articular disc being displaced, indicating a TMJ disorder.

FIG. 2 shows a TMJ disorder in which the condoyle 14 is displaced rearward within the articular fossa 18 and the articular disc 20 is displaced as well. This misalignment can be caused by a number of problems, and often the underlying problem is misalignment of teeth or occlusion at an improper bite angle that forces the condoyle 14 from a healthy position that allows full range of motion without pain.

The dental appliance 30 of the present invention serves the purpose of facilitating alignment of the upper jaw 32 and lower jaw 34. The dental appliance 30 aligns teeth on a first arch 36 with teeth on the opposing teeth on a second arch 38. The first arch of teeth 36 correspond to the maxillary arch and the second arch of teeth 38 is the mandibular arch. Hereinafter, the first arch of teeth 36 will be referred to as the maxillary arch 36, and the second arch of teeth 38 will be referred to as the mandibular arch 38

Figure 11:
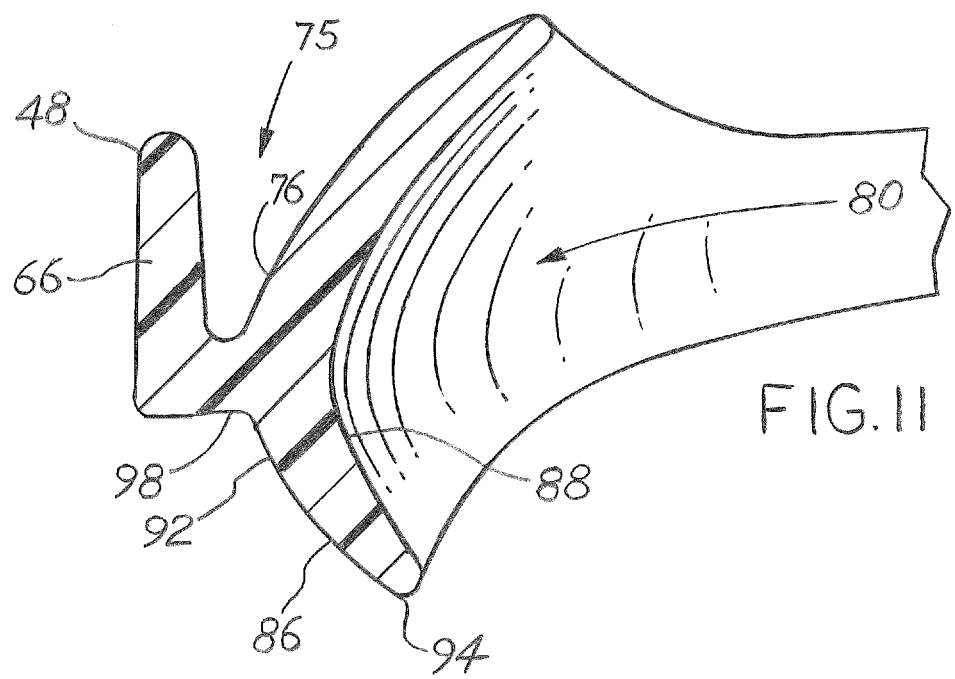
FIG. 11 is a magnified view of area 11, as shown in FIG. 5.

The dental appliance 30 has an arch plate 40 having a chewing surface portion 42 having a thickness enough to be substantially rigid. The chewing surface portion 42 is the portion of the arch plate 40 that is adapted for resting on the chewing surfaces of teeth and being between teeth on opposing arches 36, 38 as described below. The chewing surface portion 42 has a tooth contacting surface 44 on one side and an outer surface 45 on the opposite side, and the distance between the tooth contacting surface 44 and outer surface 45 defines the thickness of the chewing surface portion 42. An inner sidewall 46 is upstanding and extends away from the chewing surface portion 42. An outer sidewall 48 extends away from the chewing surface portion 42 and is spaced oppositely from the inner sidewall 46. The inner sidewall 46, tooth contacting surface 44, and outer sidewall 48 cooperate to form a tooth receiving cavity 54 that is adapted for a complementary fit with the teeth on the maxillary arch 36. The outer surface 45, opposite the tooth contacting surface 44, has relatively high points 60 that generally form a plane 62. The high points 60 correspond to the features that are present on the tooth contacting surface 44. The tooth receiving cavity 54 has an anterior end 66 that is adapted to receive upper incisors 68 and posterior ends 72 that are adapted to receive back teeth 74 on the maxillary arch 36. Within the tooth receiving cavity 54 near the anterior end 66 is an incisor valley 75. The incisor valley 75 is located between the outer sidewall 48 and a rear incisor contacting surface 76 on the inner sidewall 46. The incisor valley 75 is best seen in FIG. 11. The rear incisor contacting surface 76 is adapted to contact the rear surface of incisors on the maxillary arch 36.

Figure 3:
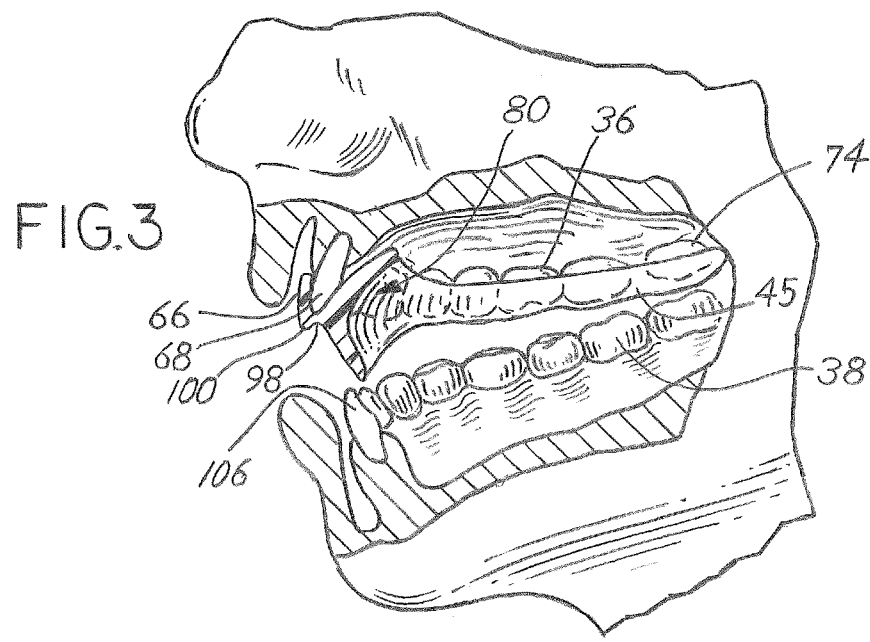
FIG. 3 is a sectional view of a maxillary arch and mandibular arch with the jaw open and the dental appliance of the present invention in place on the maxillary arch.
Figure 4:
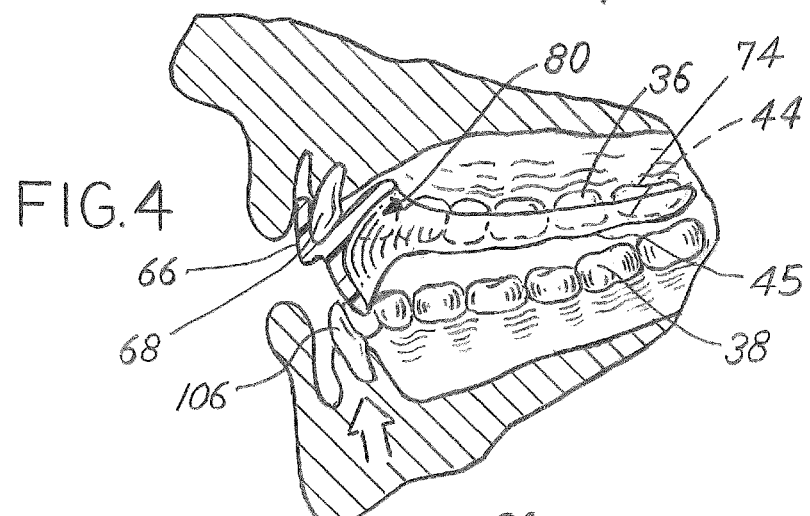
FIG. 4 is the sectional view of FIG. 3 with the jaw in a more closed position.
Figure 5:
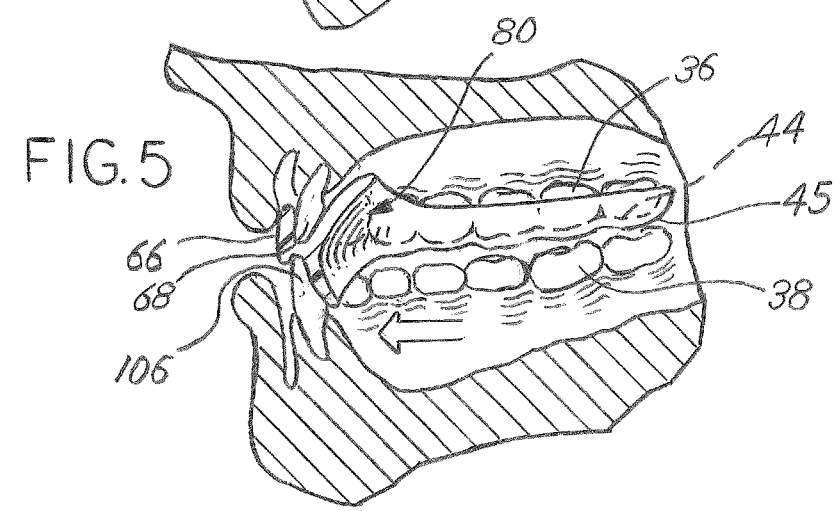
FIG. 5 is the sectional view of FIG. 4 with the jaw fully closed and teeth resting on the dental appliance of the present invention.
Figure 10:
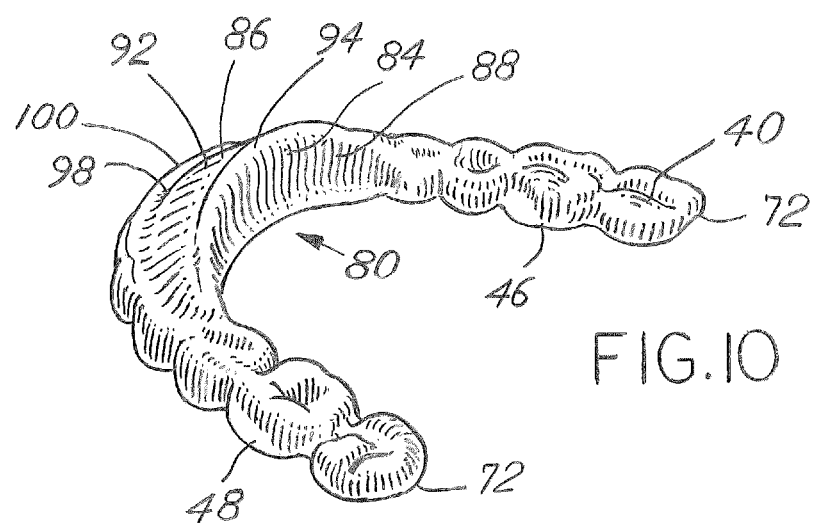
FIG. 10 is s perspective view of the dental appliance shown in FIG. 6 from the opposite side as that shown in FIG. 6.

A tongue pocket 80 is integrally molded and connected to the inner sidewall 46. The tongue pocket 80 has an upper portion 84 that extends in the same direction as the inner sidewall 46 being integrally joined thereto, which is above the plane 62 and above the tooth contacting surface 44. The tongue pocket 80 also has lower portion 86 that extends oppositely of the inner and outer sidewalls 46, 48, which is below the plane 62. An inner surface 88 of the tongue pocket 80 faces the posterior ends 72. The inner surface 88 of the tongue pocket 80 is generally concave in all directions. Particularly, the inner surface 88 of the tongue pocket 80 is concave across the plane 62, and is concave in a direction perpendicular to the plane 62. The tongue pocket 80 has an outer ramped surface 92 that is opposite the inner surface 88 as shown in FIGS. 3-5. The outer ramped surface 92 is located on the lower portion 86 of the tongue pocket 80. The outer ramped surface 92 has a lower edge 94 that defines the farthest and lowermost location with respect to the plane 62. The lower edge 94 has a smaller radius of curvature than portions of the outer ramped surface 92 nearer the plane 62. The outer ramped surface 92 is convex across the plane 62 and perpendicular to the plane 62. Opposite the lower edge 94, the outer ramped surface 92 terminates in an incisal step 98 that is adapted to receive incisors on the mandibular arch 38. The incisal step 98 is typically slightly behind the outer sidewall 48 near the anterior end 66. The outer sidewall 48 forms an anterior ridge 100 of the incisal step 98, and the incisal step 98 may slightly depressed with respect to the anterior ridge 100. The incisal step 98 is typically directly opposite the incisor valley 75 so that both are aligned on opposite sides of the tooth receiving cavity 54. The incisal step 98 begins where the outer ramped surface 92 ends. It is also contemplated that the incisal step 98 can be a flat area immediately adjacent to the end of the outer ramped surface 92, and in this case, there will be no anterior ridge 100. This is shown in FIG. 11. Although the incisal step 98 is typically directly opposite the incisor valley 75, it may be the case that the two are opposite to each other and slightly offset with respect to the anterior and posterior ends 66, 72. In some cases, it may be more comfortable for a patient to have opposing incisors held in a position that is not directly aligned. The appliance 30 will hold the incisors 68, 106 in their corresponding incisor valley 75 and incisal step 98 and a slight shift from direct alignment may be most comfortable during a patient's use of the appliance 30. The appliance 30 of the present invention is typically to be made of a durable plastic material of sufficient rigidity to tolerate to forces of being placed between teeth on opposing arches.

In use, the dental appliance 30 is adapted to align jaws 32, 34 of a patient. This tooth receiving cavity 54 is placed over the teeth of the maxillary arch 36 and the appliance 30 is pressed onto the teeth as shown in FIG. 3. Once the appliance 30 is fitted onto the teeth of the maxillary arch 36, the tooth receiving cavity 54 complementarily fits over the teeth because the tooth receiving cavity 54 has been formed previously in an impression process. During the impression process, a patient will rest their chin close to the chest, and this will set the alignment for the upper and lower incisors 68, 106. In most cases, this will align the upper and lower incisors 68, 106 directly across from each other, but in some cases direct alignment will not be the most comfortable for the patient, and when that is the case, the incisor valley 75 and incisal step 98 will be slightly offset as described above. In its placed configuration, the appliance 30 cradles the upper incisors 68 within the incisor valley 75. In the position shown in FIG. 3, the appliance 30 is fixed with respect to the maxillary arch 36. When a patient using the appliance 30 begins to bite down as shown in FIG. 4, the lower incisors 106 ride against the outer ramped surface 92. Because the outer ramped surface 92 is convex in a direction perpendicular to the plane 62 and this corresponds to vertical movement of the lower jaw 34, the lower incisors 106 are guided into a centered position with respect to the upper jaw 32. Additionally, as the lower incisors 106 ride on the outer ramped surface 92, the lower jaw 32 moves forward along the convex outer ramped surface 92. Because of the centering action and the forward shift of the lower jaw 34 caused by the lower incisors 106 riding along the outer ramped surface 92, the condoyle 14 is shifted into a healthier position that also allows for the surrounding muscles that actuate the jaw 34 to relax. FIG. 5 shows the upper and lower jaws 32, 34 together as much as possible with the appliance 30 in place. In this position, the upper and lower incisors 68, 106 are aligned. The lower incisors 68 are prevented from moving rearward with respect to the maxillary arch 36 due to the ramped outer surface 92. Further, forward movement of the lower incisors 106 with respect to the maxillary arch 36 is prevented by anterior ridge 100 that tends to keep the lower incisors 106 within the incisal step 98. The fixing of upper and lower jaws 32, 34 with respect to each other works to alleviate TMJ disorders as well as reduce bruxism particularly during sleep that result in subluxation or damage to tooth enamel.

The present invention is not limited to the description above, but may be modified within the scope of the following claims.

What is claimed is:

1. A therapeutic dental appliance for correcting TMJ in a user having upper incisors and lower incisors, said appliance comprising:

a rigid arch plate having a chewing surface portion with a tooth contacting surface, an inner sidewall extending away from said chewing surface portion, and an outer sidewall extending away from said chewing surface portion spaced oppositely from said inner sidewall, said inner and outer sidewalls and said chewing surface portion forming a tooth receiving cavity adapted for complementary receiving teeth on a first arch of teeth in a mouth and fixing said arch plate with respect to said teeth on said first arch, an outer surface of said chewing surface portion defining a plane formed by high points on said outer surface opposite said tooth contacting surface of said chewing surface portion, said tooth receiving cavity having an anterior end adapted to receive front teeth on said first arch and posterior ends adapted to receive back teeth of said first arch;

a tongue pocket affixed near said anterior end having an upper portion connected to said inner sidewall and extending in the direction of said sidewalls, and a lower portion extending oppositely of said sidewalls and beyond said plane, said tongue pocket having an inner surface being concave across said plane and concave orthogonal to said plane, said tongue pocket having an outer ramped surface on its lower portion opposite said inner surface of said tongue pocket, said outer ramped surface being convex across said plane and convex orthogonal to said plane, said outer ramped surface terminating in an incisal step opposite said anterior end of said tooth receiving cavity, said incisal step adapted for receiving incisor teeth on a second arch opposite said first arch, said outer ramped surface and a rear incisor contacting surface aligned where said outer ramped surface meets said incisal step and said rear incisor contacting surface meets an incisor valley; and when said user bites down on said dental appliance, said lower incisors contact said outer ramped surface on said lower portion to move said user's mandible forward to align said upper incisors to said lower incisors when said lower incisors contact said incisal step and said upper incisors are located in said incisor valley.

2. The therapeutic dental appliance as claimed in claim 1, said anterior end of said tooth receiving cavity having said incisor valley, said incisal step being aligned opposite said incisor valley.

3. The therapeutic dental appliance as claimed in claim 2, wherein said first arch is a maxillary arch and said second arch is a mandibular arch, said outer ramped surface adapted for guiding said mandibular arch forward with respect to said maxillary arch when incisors on said mandibular arch engage said outer ramped surface.

4. The therapeutic dental appliance as claimed in claim 2, wherein said first arch is a maxillary arch and said second arch is a mandibular arch, said outer ramped surface adapted for guiding said mandibular arch forward with respect to said maxillary arch when incisors on said mandibular arch engage said outer ramped surface.

5. The therapeutic dental appliance as claimed in claim 1, said anterior end of said tooth receiving cavity having said incisor valley and rear incisor contacting surface adjacent to said incisor valley, said outer ramped surface terminating in alignment and opposite to said rear incisor contacting surface.

6. A therapeutic dental appliance for correcting TMJ, said appliance comprising:

a rigid arch plate having a chewing surface portion with a tooth contacting surface, an inner sidewall extending away from said chewing surface portion, and an outer sidewall extending away from said chewing surface portion spaced oppositely from said inner sidewall, said inner and outer sidewalls and said chewing surface portion forming a tooth receiving cavity adapted for complementary receiving teeth on a first arch of teeth in a mouth and fixing said arch plate with respect to said teeth on said first arch, an outer surface of said chewing surface portion defining a plane formed by high points on said outer surface opposite said tooth contacting surface of said chewing surface portion, said tooth receiving cavity having an anterior end adapted to receive front teeth on said first arch and posterior ends adapted to receive back teeth of said first arch;

a tongue pocket affixed near said anterior end having an upper portion connected to said inner sidewall and extending in the direction of said sidewalls and portion of said tongue pocket within said tooth receiving cavity including a rear incisor contacting surface, and a lower portion extending oppositely of said sidewalls and beyond said plane, said tongue pocket having an inner surface being concave across said plane and concave orthogonal to said plane, said tongue pocket having an outer ramped surface on its lower portion opposite said inner surface of said tongue pocket, said outer ramped surface being convex across said plane and convex orthogonal to said plane, said outer ramped surface terminating opposite to said rear incisor contacting surface and terminating in alignment with said rear incisor contacting surface, said outer ramped surface and said rear incisor contacting surface aligned where said outer ramped surface meets an incisal step and said rear incisor contacting surface meets an incisor valley; and when said user bites down on said dental appliance, said lower incisors contact said outer ramped surface on said lower portion to move said user's mandible forward to align said upper incisors to said lower incisors when said lower incisors contact said incisal step and said upper incisors are located in said incisor valley.

7. The therapeutic dental appliance as claimed in claim 6, wherein said tooth receiving cavity includes an incisor valley located between said outer sidewall and said rear incisor contacting surface.

8. The therapeutic dental appliance as claimed in claim 7, wherein said first arch is a maxillary arch and said second arch is a mandibular arch, said outer ramped surface adapted for guiding said mandibular arch forward with respect to said maxillary arch when incisors on said mandibular arch engage said outer ramped surface.

* * * * *